(12) United States Patent
DeWall

(10) Patent No.: US 11,389,346 B2
(45) Date of Patent: Jul. 19, 2022

(54) SKIN COMPRESSION DEVICE AND METHODS OF PRODUCTION AND USE THEREOF

(71) Applicant: DePuy Synthes Prodcuts, Inc., Raynham, MA (US)

(72) Inventor: Ryan DeWall, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 249 days.

(21) Appl. No.: 16/547,865

(22) Filed: Aug. 22, 2019

(65) Prior Publication Data
US 2021/0052441 A1    Feb. 25, 2021

(51) Int. Cl.
*A61F 15/00* (2006.01)
*A61B 17/60* (2006.01)

(52) U.S. Cl.
CPC ............ *A61F 15/008* (2013.01); *A61B 17/60* (2013.01)

(58) Field of Classification Search
CPC ....... A61B 17/08; A61B 17/085; A61B 17/58; A61B 17/60; A61F 2013/0028; A61F 15/008; A61F 13/02; A61F 13/00021; A61F 13/00029; A61F 13/00038; A61F 13/00063; A61F 13/023; A61F 13/0233; A61F 13/0246; A61F 13/0226; A61F 2013/00217; A61F 2013/00225; A61F 2013/00234; A61F 2013/00451; A61F 2013/00544; A61F 2013/00561; A61F 2013/0037; A61F 2013/00374; A61F 2013/00387; A45D 44/22

USPC .................. 128/888; 602/42, 52–54, 57, 43; 606/204.45
See application file for complete search history.

(56) References Cited

U.S. PATENT DOCUMENTS

| | | | |
|---|---|---|---|
| 7,834,232 B2 | 11/2010 | Rastegar et al. | |
| 8,389,791 B2 | 3/2013 | Gurtner et al. | |
| 9,913,758 B2 | 3/2018 | Rastegar et al. | |
| 2012/0221044 A1* | 8/2012 | Archibald ............ | A61B 17/085 606/214 |
| 2013/0237895 A1* | 9/2013 | Rastegar ............ | A61F 13/00038 602/53 |

(Continued)

FOREIGN PATENT DOCUMENTS

WO        2013038182 A2    3/2013

OTHER PUBLICATIONS

Ahmad, et al.; "Feasibility Study of Polyurethane Shape-Memory Polymer Actuators for Pressure Bandage Application," Science and Technology of Advanced Materials; (2012), vol. 13, pp. 1-7.

(Continued)

*Primary Examiner* — Rachael E Bredefeld
*Assistant Examiner* — Trisha Talapatra
(74) *Attorney, Agent, or Firm* — Dunlap Codding, P.C.

(57) ABSTRACT

Skin compression devices are disclosed that are formed of a shape memory material and that have multiple tensioning members. Disposal of one or more skin compression devices on the skin of a subject increases the temperature of the shape memory material and causes the tensioning members to bend inward, thereby compressing the area of skin disposed between the tensioning members; this compression shields the compressed skin from tensile loading. Methods of production and use of the skin compression devices are also disclosed.

15 Claims, 3 Drawing Sheets

(56) References Cited

U.S. PATENT DOCUMENTS

| | | | |
|---|---|---|---|
| 2014/0128819 A1* | 5/2014 | Eaves | A61B 17/085 604/264 |
| 2018/0185196 A1 | 7/2018 | Levinson et al. | |
| 2019/0015255 A1 | 1/2019 | Gurtner et al. | |
| 2020/0246193 A1* | 8/2020 | Wurapa | A61F 13/0259 |

OTHER PUBLICATIONS

Kumar, et al.; "Memory Bandage for Functional Compression Management for Venous Ulcers," Fibers; (2016), vol. 4, pp. 1-10.
Kazmers, et al.; "Prevention of Pin Site Infection in External Fixation: A Review of the Literature," Strat Traum Recon (2016), vol. 11, pp. 75-85.

* cited by examiner

SKIN COMPRESSION DEVICE AND METHODS OF PRODUCTION AND USE THEREOF

CROSS REFERENCE TO RELATED APPLICATIONS/INCORPORATION BY REFERENCE STATEMENT

Not Applicable.

STATEMENT REGARDING FEDERALLY SPONSORED RESEARCH OR DEVELOPMENT

Not Applicable.

BACKGROUND

Percutaneous devices, such as (but not limited to) pins, screws, and wires, are commonly used in orthopedic procedures to stabilize and/or correct fractures, injuries, and defects. Particular examples of percutaneous devices include (but are not limited to) skeletal traction pins, percutaneous fracture pinning, and external fixation devices. However, these devices can cause excessive skin tension at their insertion sites, and this tension can decrease blood supply and lead to necrosis of the surrounding tissue, thus increasing the possibility of infection at the insertion site. One study reported site infection as the most common complication of external fixation, with an up to 100% infection rate in the study group (Kazmers et al., *Strat Traum Limb Recon* (2016) 11:75-85). As such, new and improved methods of preventing excessive skin tension around the insertion sites of percutaneous devices are desired to reduce infection related thereto.

Similarly, other types of skin wounds (including wounds resulting from injuries as well as surgically created wounds (i.e., incision sites)) also cause excessive skin tension. As such, bandages and dressings applied to these wounds need to apply a certain amount of pressure to close the wound and keep it closed, so as to decrease the excessive skin tension around the wound.

Therefore, there is a need in the art for new and improved devices and methods of using same to decrease excessive skin tension, such as (but not limited to) around percutaneous insertion sites and wounds. It is to such devices, as well as methods of producing and using same, that the present disclosure is directed.

DETAILED DESCRIPTION

Before explaining at least one embodiment of the present disclosure in detail by way of exemplary language and results, it is to be understood that the present disclosure is not limited in its application to the details of construction and the arrangement of the components set forth in the following description. The present disclosure is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the medical procedures and techniques of, surgery, anesthesia, wound healing, and infectious control described herein are those well-known and commonly used in the art. Standard techniques are used for infection diagnostic and therapeutic application.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles, compositions, kits, and/or methods disclosed herein can be made and executed without undue experimentation in light of the present disclosure. While the articles, compositions, kits, and/or methods have been described in terms of particular embodiments, it will be apparent to those of skill in the art that variations may be applied to the articles, compositions, kits, and/or methods and in the steps or in the sequence of steps of the methods described herein without departing from the concept, spirit, and scope of the present disclosure. All such similar substitutes and modifications apparent to those skilled in the art are deemed to be within the spirit, scope, and concept of the present disclosure as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

As used herein, the phrases "associated with" and "coupled to" include both direct association/binding of two moieties to one another as well as indirect association/binding of two moieties to one another. Non-limiting examples of associations/couplings include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety, for example.

As used herein, the term "patient" or "subject" is meant to include all organisms, whether alive or dead, including any species having soft tissues and bones. For example, a method according to the inventive concepts disclosed herein may be used to apply a skin compression device to a living human, horse, cow, sheep, cat, dog, and the like.

The term "ambient temperature" as used herein refers to a temperature of the air surrounding a skin of a subject. That is, the "ambient temperature" is the temperature of the subject's environment. When located indoors, the ambient temperature is typically in a range of from about 60° F. to about 80° F. However, when the subject is located outdoors, the ambient temperature may be greater than or less than the above range. For the devices taught herein to be effective upon application to the skin, the ambient temperature should be sufficiently below body temperature (i.e., 98.6° F.) at the time of application of the device to the skin; otherwise, the skin compression device will not adequately function in accordance with the present disclosure.

Certain non-limiting embodiments of the present disclosure are directed to a skin compression device for shielding a skin of a subject from tensile loading. The skin compression device includes at least two tensioning members formed of a shape memory material, such as (but not limited to) a shape memory alloy. Each tensioning member has a first end and a second end, wherein the first end of a first tensioning member and the first end of a second tensioning member are directly or indirectly connected to one another; in addition, the second end of the first tensioning member is disposed a distance from the second end of the second tensioning member. Disposal of the skin compression device on the skin increases the temperature of the shape memory material (i.e., shape memory alloy), thereby causing the first and second tensioning members to deform and move toward one another and thus compress the area of skin disposed between the first and second tensioning members.

In a particular (but non-limiting) embodiment, the skin compression device further includes a bonding material applied to at least a portion of a surface of the at least two tensioning members for adhering the skin compression device to the skin of the subject. In a particular (but non-limiting) embodiment, the bonding material comprises a skin adhesive or glue or at least one structural bonding material (such as, but not limited to, a suture, staple, or barb-type element).

In a particular (but non-limiting) embodiment, the shape memory alloy from which at least a portion of the skin compression device is formed is a nickel-titanium alloy, such as (but not limited to) nitinol.

In a particular (but non-limiting) embodiment, the skin compression device includes the first tensioning member, the second tensioning member, and a supporting member that indirectly connects the first end of the first tensioning member to the first end of the second tensioning member; in particular, the supporting member has a first end that is connected to the first end of the first tensioning member and a second end that is connected to the first end of the second tensioning member. In one (non-limiting) embodiment, the first and second tensioning members are disposed substantially parallel to one another such that the skin compression device is substantially bracket- or U-shaped. Alternatively, the first and second tensioning members can extend from the supporting member at an angle greater than 90°.

In a particular (but non-limiting) embodiment, the first and second tensioning members are directly connected to one another such that the first end of the first tensioning member is connected to the first end of the second tensioning member, and wherein the skin compression device is substantially arc-shaped or V-shaped.

In a particular (but non-limiting) embodiment, the skin compression device further includes an antimicrobial agent associated therewith. For example (but not by way of limitation), the antimicrobial agent may be disposed on a film that extends from at least a portion of the first tensioning member to at least a portion of the second tensioning member. Alternatively (and/or in addition thereto), the film may extend from at least a portion of the supporting member, if present.

Certain non-limiting embodiments of the present disclosure are directed to an assembly that comprises two or more of any of the skin compression devices described or otherwise contemplated herein.

Certain non-limiting embodiments of the present disclosure are directed to a method of treating a subject. In the method, at least one of any of the skin compression devices disclosed or otherwise contemplated herein (including an assembly of two or more of the skin compression devices disclosed or otherwise contemplated herein) is affixed to the skin of the subject, wherein a surface temperature of the skin of the subject is greater than an ambient temperature. The surface temperature of the skin is then allowed to increase the temperature of the at least one shape memory material (i.e., shape memory alloy) from which at least a portion of the skin compression device is formed, thereby causing the first and second tensioning members to deform and move toward one another and thus compress the area of skin disposed between the first and second tensioning members to shield the compressed skin from tensile loading.

In a particular (but non-limiting) embodiment, the area of skin disposed between the first and second tensioning members comprises a wound. Alternatively (and/or in addition thereto), the area of skin disposed between the first and second tensioning members has at least one percutaneous device extending therethrough.

In a particular (but non-limiting) embodiment, two or more skin compression devices are affixed to the skin of the subject. In this manner, a larger area of skin can be compressed between the two or more skin compression devices (as described in greater detail herein below).

Certain non-limiting embodiments of the present disclosure include a kit containing one or more of any of the skin compression devices described or otherwise contemplated herein (including, but not limited to, an assembly comprising two or more of any of the skin compression devices described or otherwise contemplated herein). In addition, the kit may further include one or more additional reagents that can be utilized with the skin compression device(s). For example, but not by way of limitation, the kit may include one or more skin compression devices in combination with a bonding material and/or an antimicrobial agent. The bonding material and/or antimicrobial agent may be applied to or otherwise associated with the skin compression device(s) prior to disposal in the kit, or the bonding material and/or antimicrobial agent may be disposed in the kit separate from the skin compression devices (such as, but not limited to, in separate containers or compartments of the kit). The relative numbers and amounts of skin compression devices, bonding materials, and/or antimicrobial agents present in the kit can vary widely. Also, when multiple skin compression devices are present, the skin compression devices may have the same shape and size or different shapes and sizes. In addition, the kit can further include a set of written instructions explaining how to use the kit. A kit of this nature can be used in any of the methods described or otherwise contemplated herein.

Figure 1:
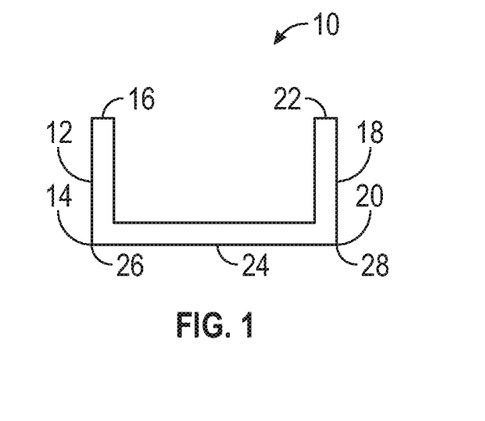
FIG. 1 is a perspective view of a first, non-limiting embodiment of a skin compression device constructed in accordance with the present disclosure.

Turning now to the Drawings, and in particular to FIG. 1, shown therein is a skin compression device 10 constructed in accordance with the present disclosure. The skin compression device 10 includes a first tensioning member 12 that has a first end 14 and a second end 16. The skin compression device 10 also includes a second tensioning member 18 that has a first end 20 and a second end 22. The second end 16 of the first tensioning member 12 is disposed a distance from the second end 22 of the second tensioning member 18.

In the embodiment of FIG. 1, the skin compression device 10 further includes a supporting member 24 that has a first end 26 and a second end 28. The supporting member 24 indirectly connects the first end 14 of the first tensioning member 12 to the first end 20 of the second tensioning member 18; that is, the first end 26 of the supporting member 24 is connected to the first end 14 of the first tensioning member 12, and the second end 28 of the supporting member 24 is connected to the first end 20 of the second tensioning member 18.

The skin compression device 10 can be formed of any material that has shape memory and that allows the device to function in accordance with the present disclosure. That is, the skin of a subject has a surface temperature that is greater than an ambient temperature of the surrounding air, and the shape memory material from which the skin compression device 10 is formed should be capable of deforming at skin surface temperature, as described in greater detail herein below.

In certain non-limiting embodiments, at least a portion of the skin compression device 10 is formed of a shape memory alloy, such as (but not limited to) alloys containing at least one of nickel, titanium, zinc, copper, gold, silver, platinum, aluminum, iron, manganese, gallium, tin, silicon, cadmium, cobalt, or palladium. Non-limiting examples of various shape memory alloys that can be utilized in accordance with the present disclosure are disclosed in Patent Application Publication No. US 2018/0185196 (published Jul. 5, 2018).

In a particular (but non-limiting) embodiment, at least a portion of the skin compression device is formed of a nickel-titanium alloy. One non-limiting example of a nickel-titanium alloy that can be utilized in accordance with the present disclosure is nitinol.

In addition, it will be understood that the skin compression devices taught therein are not limited to solely being formed of a shape memory material. Rather, only a portion of the skin compression device may be formed of the shape memory material, and another portion of the skin compression device may be formed of a non-shape memory material. For example, at least a portion (or all) of one or both of the two tensioning members 12 and 18 of the skin compression device 10 may be formed of a shape memory material, while a portion or all of the supporting member 24 may be formed of a non-shape memory material. In another non-limiting embodiment, only a portion of one or both of the two tensioning members 12 and 18 is formed of a shape memory material, and another portion of one or both of the two tensioning members 12 and 18 is formed of a non-shape memory material. Alternatively, the entire skin compression device 10 may be formed of a shape memory material.

The skin compression devices of the present disclosure may have any shape that allows the device to function in accordance with the present disclosure. Several different shapes are depicted and described herein; however, it will be understood that these different shapes are provided for purposes of example only. The skin compression devices of the present disclosure may assume any shapes contemplatable by a person having ordinary skill in the art; as such, all contemplatable shapes fall within the scope of the present disclosure.

In the skin compression device 10, the first and second tensioning members 16 and 22 are illustrated as being disposed substantially parallel to one another such that the skin compression device 10 is substantially bracket- or U-shaped. However, this particular structure is but one embodiment of shapes that can be assumed by the skin compression devices taught herein; other specific (but non-limiting) shapes of skin compression devices that fall within the scope of the present disclosure are described in greater detail herein below with respect to FIGS. 6, 9, 12, etc. In addition, while the supporting member 24 is depicted in FIG. 1 as being a linear member, this should not be considered limiting; it is to be understood that the supporting member may possess any size and/or shape that allows the skin compression device to function in accordance with the present disclosure.

Figure 2:
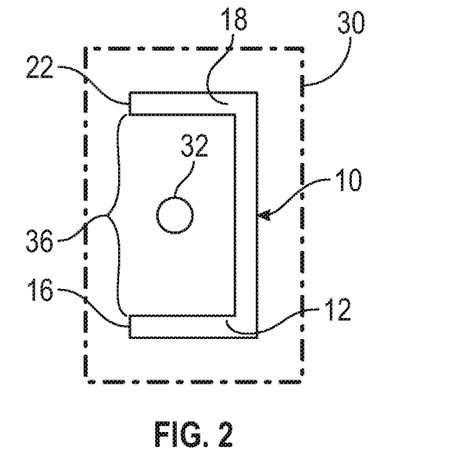
FIG. 2 is a perspective view of the skin compression device of FIG. 1 applied to the skin of a subject around a percutaneous device extending through the skin and prior to the skin compression device reaching body temperature.
Figure 3:
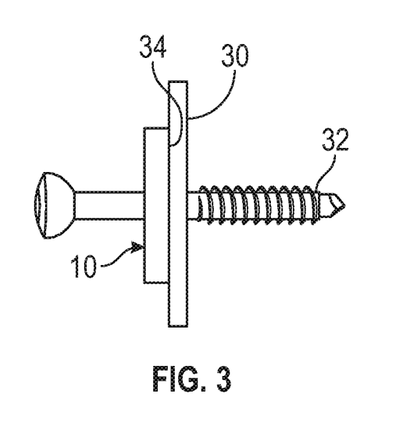
FIG. 3 is a cross sectional view of the skin compression device and percutaneous device of FIG. 2.
Figure 4:
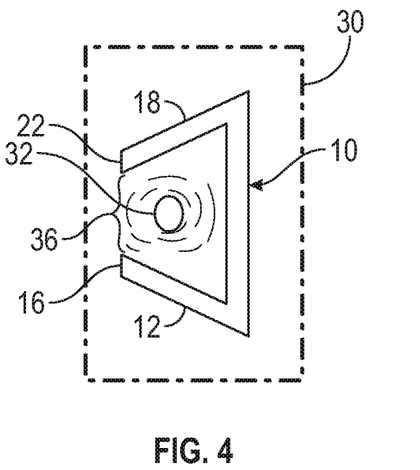
FIG. 4 is a perspective view illustrating the compression of the skin by the skin compression device of FIGS. 1-3 upon incubation of the skin compression device at body temperature.

The skin compression device 10 also includes a bonding material 34 (see FIG. 3) applied to at least a portion of a lower surface of the skin compression device 10 (such as, but not limited to, at least a portion of the first and second tensioning members 12 and 18) for adhering the skin compression device 10 to a skin 30 of a subject (FIGS. 2-4).

Any type of bonding material known in the art or otherwise contemplated herein for use in adhering the skin compression devices taught herein may be used in accordance with the present disclosure. For example (but not by way of limitation), the bonding material may be an adhesive, such as (but not limited to) a skin adhesive or skin glue. Alternatively, the bonding material may be a structural bonding material, such as, but not limited to, a suture, staple, or barb-type element.

FIGS. 2-4 depict one non-limiting use of the skin compression device 10. In FIGS. 2-3, the skin compression device 10 is applied to the skin 30 of a subject (such as, but not limited to, around a percutaneous device 32 that extends through the skin 30). In this manner, an area 36 of the skin 30 is disposed between the first and second tensioning members 12 and 18 of the skin compression device 10. As shown in FIG. 4, disposal of the skin compression device 10 on the skin 30 increases the temperature of the shape memory material from which at least a portion of the skin compression device 10 is formed; incubation of the skin compression device 10 at the skin's surface temperature for a certain period of time causes the first and second tensioning members 12 and 18 to deform and move toward one another, thereby compressing the area 36 of skin 30 disposed between the first and second tensioning members 12 and 18. In this manner, the skin compression device 10 shields the compressed skin from tensile loading.

Figure 5:
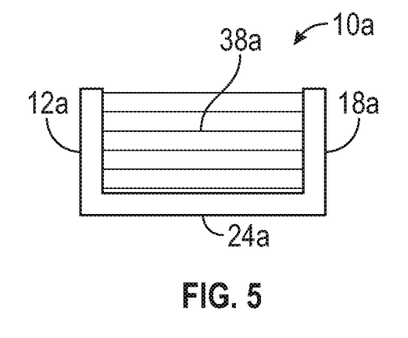
FIG. 5 is a perspective view of another non-limiting embodiment of a skin compression device constructed in accordance with the present disclosure and having an antimicrobial agent associated therewith.

FIG. 5 depicts another skin compression device constructed in accordance with the present disclosure. The skin compression device 10a of FIG. 5 is similar to the skin compression device 10 of FIGS. 1-4, except as described herein below. The skin compression device 10a has an antimicrobial agent 38a associated therewith. For example (but not by way of limitation), the antimicrobial agent 38a may be associated with at least a portion of one or more of a first tensioning member 12a, a second tensioning member 18a, and/or a supporting member 24a. FIG. 5 depicts the antimicrobial agent 38a as being disposed upon a film that extends from at least a portion of the first tensioning member 12a to at least a portion of the second tensioning member 18a. However, this application should not be construed as limiting; rather, it should be understood that the antimicrobial agent 38a may be associated with the skin compression device 10a in any manner that will ultimately allow the antimicrobial agent 38a to interact with an area of skin to be compressed by the skin compression device 10a.

Any antimicrobial agents known in the art or otherwise contemplatable by a person of ordinary skill in the art may be utilized in accordance with the present disclosure. For example (but not by way of limitation), the antimicrobial agent may be an antibacterial agent. Examples of antimicrobial and antibacterial agents are well known in the art, and a wide variety thereof are commercially available. Therefore, it is well within the common abilities of a person having ordinary skill in the art to identify and select particular antimicrobial and antibacterial agents that can be used in accordance with the present disclosure, given the particular uses for which the skin compression devices are employed. As such, no further discussion thereon is deemed necessary.

Figure 6:
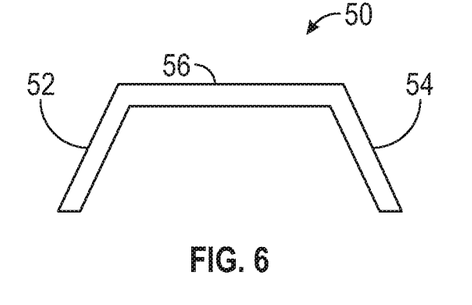
FIG. 6 is a perspective view of another non-limiting embodiment of a skin compression device constructed in accordance with the present disclosure.
Figure 7:
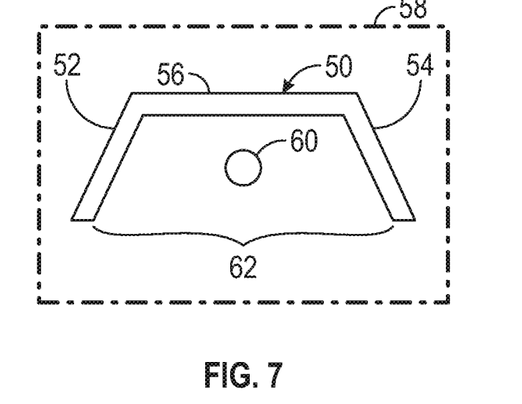
FIG. 7 is a perspective view of the skin compression device of FIG. 6 applied to the skin of a subject around a percutaneous device extending through the skin.
Figure 8:
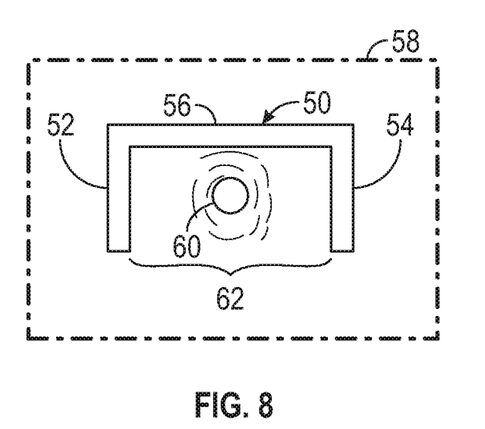
FIG. 8 is a perspective view illustrating the compression of the skin by the skin compression device of FIGS. 6-7 upon incubation of the skin compression device at body temperature.

FIGS. 6-8 depict another skin compression device constructed in accordance with the present disclosure. The skin compression device 50 of FIGS. 6-8 is similar to the skin compression device 10 of FIGS. 1-3, except as described below. The skin compression device 50 includes first and second tensioning members 52 and 54, respectively, as well as a supporting member 56. However, the skin compression device 50 differs from the skin compression device 10 in that the first and second tensioning members 52 and 54 extend from the supporting member 56 at an angle greater than 90°. As shown in FIGS. 7 and 8, when the skin compression device 50 is applied to the skin 58 of a subject (such as, but not limited to, about a percutaneous device 60 extending from the skin 58), an area 62 of the skin 58 that is compressed upon incubation of the device 50 at skin surface temperature is greater than the area 36 of skin 30 compressed by the device 10, because of the angles at which the first and second tensioning members 52 and 54 are disposed.

While the previous Figures depict skin compression devices that have two tensioning members that are indirectly connected to one another through a supporting member, it is to be understood that the two tensioning members of the skin compression devices of the present disclosure can also be directly connected to one another. That is, a first end of the first tensioning member is connected to a first end of the second tensioning member, while a second end of the first tensioning member is disposed a distance from a second end of the second tensioning member. In this manner, the skin compression device assumes a substantially linear, curved, arced, or V-shape.

Figure 9:
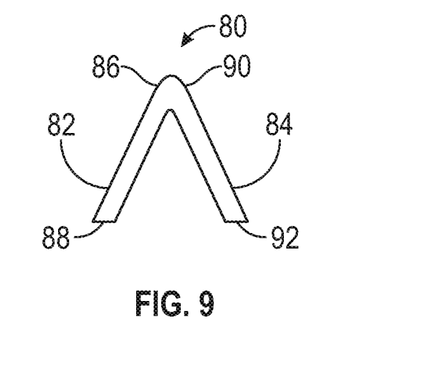
FIG. 9 is a perspective view of another non-limiting embodiment of a skin compression device constructed in accordance with the present disclosure.
Figure 10:
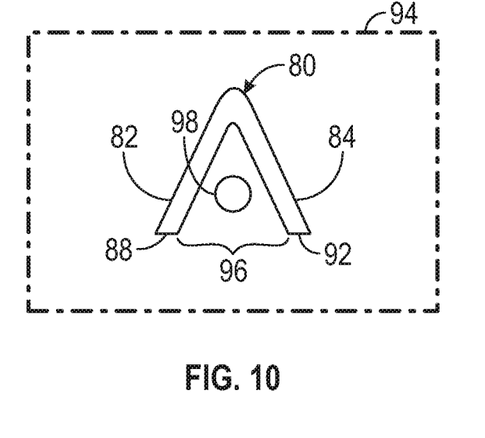
FIG. 10 is a perspective view of the skin compression device of FIG. 9 applied to the skin of a subject around a percutaneous device extending through the skin.
Figure 11:
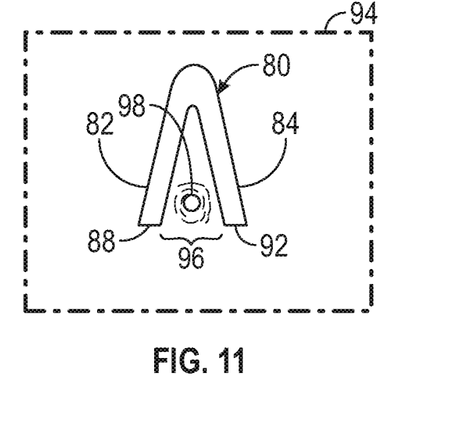
FIG. 11 is a perspective view illustrating the compression of the skin by the skin compression device of FIGS. 9-10 upon incubation of the skin compression device at body temperature.

For example, FIGS. 9-11 depict another skin compression device 80 that does not include a supporting member; rather, a first tensioning member 82 is directly connected to a second tensioning member 84. Specifically, a first end 86 of the first tensioning member 82 is attached to a first end 90 of the second tensioning member 84, while a second end 88 of the first tensioning member 82 is disposed a distance from a second end 92 of the second tensioning member 84. In this manner, the skin compression device assumes a substantially V-shape.

The first and second tensioning members 82 and 84 may be integrally formed (i.e., a single length of material is bent or otherwise formed (such as, but not limited to, in a V-shape or curved or arced shape) so as to be delineated into two sections that serve as the first and second tensioning members. Alternatively, there may be a separate attachment point through which the first and second tensioning members 82 and 84 are connected to one another.

As shown in FIGS. 10-11, the skin compression device 80 is applied to the skin 94 of the subject (such as, but not limited to, around a percutaneous device 98 that extends through the skin 94). In this manner, an area 96 of the skin 94 is disposed between the first and second tensioning members 82 and 84 of the skin compression device 80. Disposal of the skin compression device 80 on the skin 94 increases the temperature of the shape memory material from which at least a portion of the skin compression device 80 is formed; incubation at the skin's surface temperature for a certain period of time causes the first and second tensioning members 82 and 84 to deform and move toward one another, thereby compressing the area 96 of skin 94 disposed between the first and second tensioning members 82 and 84. In this manner, the skin compression device 80 shields the compressed skin from tensile loading.

Figure 12:
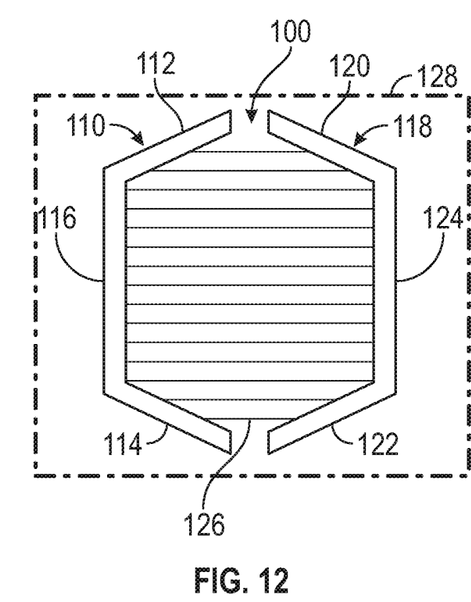
FIG. 12 is a perspective view of an assembly of two skin compression devices constructed in accordance with the present disclosure and having an antimicrobial agent associated therewith.
Figure 13:
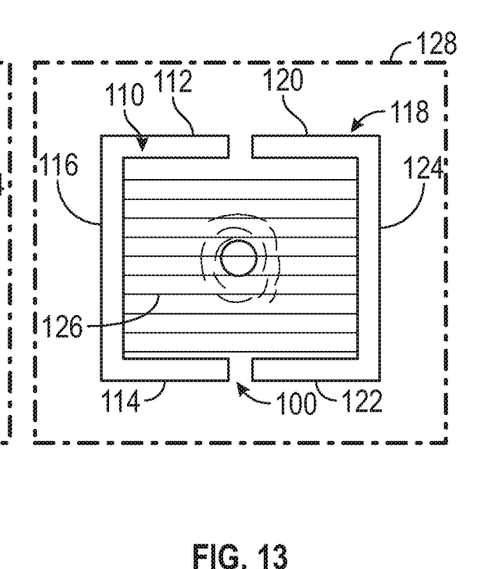
FIG. 13 is a perspective view illustrating the compression of skin by the two skin compression devices of FIG. 12 upon incubation of the skin compression device at body temperature.

While FIGS. 1-11 depict application of a single skin compression device, it will be understood that multiple skin compression devices may be utilized together, such as (but not limited to) in the form of an assembly. FIG. 12-13 illustrate the use of two skin compression devices similar to the skin compression device 50 of FIGS. 6-8 in an assembly 100. The assembly 100 includes a first skin compression device 110 and a second skin compression device 118 that are disposed on a skin 128 of a subject in an opposing, mirrored arrangement to one another. The first skin compression device 110 has a first tensioning member 112, a second tensioning member 114, and a supporting member 116, while the second skin compression device 118 has a first tensioning member 120, a second tensioning member 122, and a supporting member 124. The skin compression devices 110 and 118 are further illustrated as having an antimicrobial agent 126 extending therebetween; however, it will be understood that the antimicrobial agent 126 may be omitted, if not desired. In addition, when the antimicrobial agent 126 is present, the antimicrobial agent 126 may be disposed on the skin 128 prior to or after application of one or both of the skin compression devices 110 and 118. Alternatively, the antimicrobial agent 126 may be associated with at least a portion of the skin compression device(s) 110 and/or 118; for example, the antimicrobial agent 126 may be disposed on a film that extends from at least a portion of the skin compression device 110 and/or the skin compression device 118.

As can be seen in FIGS. 12-13, disposal of the assembly 100 of skin compression devices 110 and 118 on the skin 128 increases the temperature of the shape memory material from which at least a portion of the skin compression devices 110 and 118 is formed; incubation at the skin's surface temperature for a certain period of time causes the first tensioning members 112 and 120 and second tensioning members 114 and 122 to deform and move toward one another, thereby compressing the area of skin 128 disposed between the first and second skin compression devices 110 and 118. In this manner, the assembly 100 of skin compression devices 110 and 118 shields the compressed skin from tensile loading.

In addition, the area of skin compressed by the assembly 100 is greater than the amount of skin compressed by a single skin compression device. Further, use of the assembly 100 of two skin compression devices 110 and 118 results in a more uniform level of compression across the entire area of skin disposed within the assembly 100, when compared to the compression patterns observed with a single skin compression device.

Figure 14:
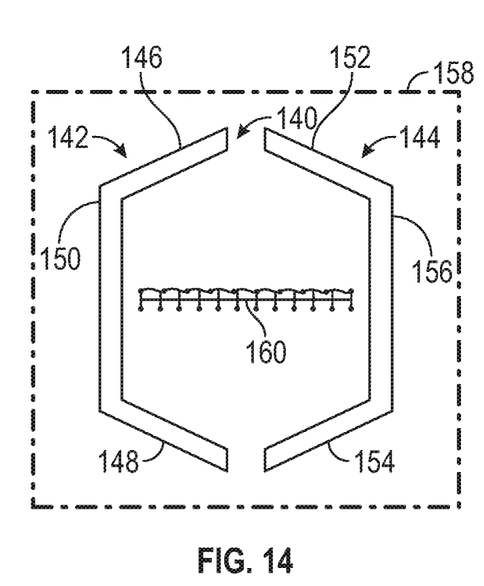
FIG. 14 is a perspective view of an assembly of two skin compression devices constructed in accordance with the present disclosure and applied to the skin of a subject around a wound therein.
Figure 15:
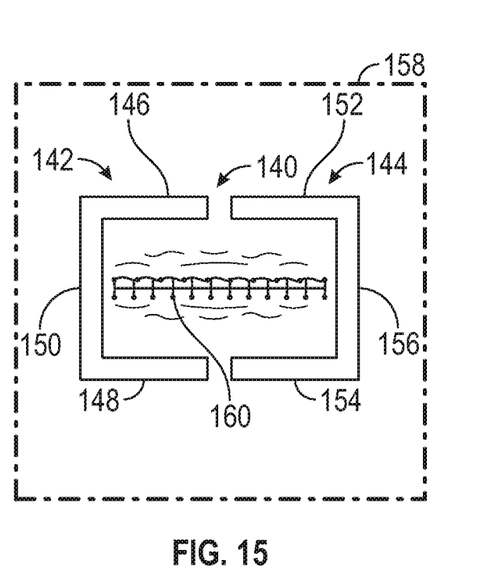
FIG. 15 is a perspective view illustrating the compression of skin by the two skin compression devices of FIG. 15 upon incubation of the skin compression device at body temperature.

While the skin compression devices shown in FIGS. 1-11 are depicted as being disposed on skin having percutaneous devices extending therethrough, it will be understood that the skin compression devices of the present disclosure are not limited to uses in this manner. Rather, the skin compression devices of the present disclosure may be utilized under any circumstance for which compression of skin/reduction of tensile loading is desired. For example (but not by way of limitation), FIGS. 12-13 depict application of the assembly 100 of the skin compression devices 110 and 118 to skin that does not have a percutaneous device extending therethrough; rather, the assembly 100 is depicted in FIGS. 12-13 as simply being utilized for application of the antimicrobial agent 126 (or other therapeutic agent) to the skin 128. Likewise, FIGS. 14-15 depict another condition under which the skin compression devices of the present disclosure may be utilized. In this condition, an assembly of skin compression devices is utilized to surround a wound extending through the skin of a subject and reduce tensile loading caused by the wound.

FIGS. 14-15 illustrate an assembly 140 that includes a first skin compression device 142 and a second skin compression device 144 that are disposed on a skin 158 of a subject in an opposing, mirrored arrangement to one another and about a wound 160. The first skin compression device 142 has a first tensioning member 146, a second tensioning member 148, and a supporting member 150, while the second skin compression device 144 has a first tensioning member 152, a second tensioning member 154, and a supporting member 156. The placement of the skin compression devices 142 and 144 allows the entire length of the wound 160 to be disposed within the assembly 140, and thus ensures a substantially uniform compression of the entire wound 160 by the assembly 140 upon incubation of the assembly 140 at skin surface temperature, as shown in FIG. 15.

While FIGS. 14-15 depict a sutured wound, it will be understood that the skin compression devices and assemblies of the present disclosure may be disposed about any type of wound known in the art (including wounds resulting from injuries and surgically created wounds, as well as both sutured and unsutured wounds). For example (but not by way of limitation), use of an assembly of skin compression devices may be especially useful to surround (and thus compress the skin surrounding) a surgically created skin defect around a penetrating foreign implant (such as a percutaneous device).

When the two tensioning members are directly connected to one another (such as, but not limited to, as shown in FIGS. 9-11), the two tensioning members may be integrally formed (i.e., a single length of material may define both tensioning members based upon the movements of the ends thereof); alternatively, the directly connected tensioning members may be formed of two different materials. When the tensioning members are indirectly connected to one another (such as, but not limited to, as shown in FIGS. 1-8 and 12-15), the tensioning members and the support member may still be integrally formed of the same material. Alternatively, the two tensioning members may be formed of a different material than the supporting member, or one of the first and second tensioning members may be formed of a different material than the supporting member and the other tensioning member. In addition, an entire length of an individual tensioning or support member need not be formed of the same material; that is, a portion of a tensioning or support member may be formed of the shape memory material, while another portion thereof may be formed of a non-shape memory material. In this embodiment, a portion of one member may be integrally formed with the connecting portion of another member so as to provide strength and/or limit movement of the joint connecting the two members. This embodiment may be useful when the two tensioning members are directly connected to one another, so as to ensure that an area is retained in between the two tensioning members following deformation of the shape memory material.

Thus, in accordance with the present disclosure, there have been provided devices, assemblies, and kits, as well as methods of producing and using same, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

What is claimed is:

1. A skin compression device for shielding a skin of a subject from tensile loading, the skin compression device comprising:
    a first tensioning member having a first end and a second end and being formed of a shape memory alloy;
    a second tensioning member having a first end and a second end and being formed of a shape memory alloy, wherein the first end of the second tensioning member is directly connected to the first end of the first tensioning member, and wherein the second end of the second tensioning member is disposed a distance from the second end of the first tensioning member such that the skin compression device is substantially V-shaped; wherein the directly connected first ends of the first and second tensioning members form an acute angle of the substantially V-shaped skin compression device; a bonding material applied to a lower surface of the first and second tensioning members for adhering the skin compression device to the skin of the subject;
    wherein the skin compression device is configured for disposal on the skin of the subject such that the first and second tensioning members adhere to a substantially V-shaped area of skin; and
    wherein disposal of the skin compression device on the skin increases the temperature of the shape memory alloy, thereby causing the first and second tensioning members to deform and move toward one another and thus compress the substantially V-shaped area of skin disposed between the first and second tensioning members.

2. The skin compression device of claim 1, wherein the shape memory alloy is a nickel-titanium alloy.

3. The skin compression device of claim 2, wherein the nickel-titanium alloy is nitinol.

4. The skin compression device of claim 1, further comprising an antimicrobial agent associated therewith.

5. An assembly comprising two or more of the skin compression devices of claim 1.

6. A method of treating a subject, the method comprising the steps of:
    affixing at least one skin compression device of claim 1 to the skin of the subject, wherein a surface temperature of the skin of the subject is greater than an ambient temperature; and
    allowing the temperature of the skin to increase the temperature of the shape memory alloy of the skin compression device, thereby causing the first and second tensioning members to deform and move toward one another and thus compress the area of skin disposed between the first and second tensioning members to shield the compressed skin from tensile loading.

7. The method of claim 6, wherein the area of skin disposed between the first and second tensioning members comprises a wound.

8. The method of claim 6, wherein the area of skin disposed between the first and second tensioning members has at least one percutaneous device extending therethrough.

9. The method of claim 6, wherein the shape memory alloy of the first and second tensioning members is a nickel-titanium alloy.

10. The method of claim 9, wherein the nickel-titanium alloy is nitinol.

11. The method of claim 6, wherein the at least one skin compression device further comprises an antimicrobial agent associated therewith.

12. The method of claim 6, wherein the step of affixing is further defined as affixing two skin compression devices to the skin of the subject.

13. A kit, comprising:
   at least one skin compression device of claim 1; and
   a bonding material for adhering the at least one skin compression device to the skin of a subject.

14. The kit of claim 13, further defined as comprising a plurality of skin compression devices.

15. The kit of claim 13, further comprising an antimicrobial agent.

* * * * *